(12) United States Patent
Sharp et al.

(10) Patent No.: US 8,025,670 B2
(45) Date of Patent: Sep. 27, 2011

(54) METHODS AND APPARATUS FOR NATURAL ORIFICE VAGINAL HYSTERECTOMY

(75) Inventors: Bradley J. Sharp, Irvine, CA (US);
Stephen Graham Bell, Rome (IT);
Wayne A. Noda, Mission Viejo, CA (US); Elbert Y. Tzeng, Irvine, CA (US)

(73) Assignee: Minos Medical, Irvine, CA (US)

( * ) Notice: Subject to any disclaimer, the term of this patent is extended or adjusted under 35 U.S.C. 154(b) by 281 days.

(21) Appl. No.: 11/870,884

(22) Filed: Oct. 11, 2007

(65) Prior Publication Data
US 2008/0119868 A1 May 22, 2008

Related U.S. Application Data

(60) Provisional application No. 60/867,061, filed on Nov. 22, 2006.

(51) Int. Cl.
*A61D 1/06* (2006.01)

(52) U.S. Cl. ......... 606/137; 606/119; 606/135; 128/842

(58) Field of Classification Search .................. 606/119, 606/135, 137; 128/842
See application file for complete search history.

(56) References Cited

U.S. PATENT DOCUMENTS

| | | | |
|---|---|---|---|
| 5,449,370 A | 9/1995 | Vaitekunas | |
| 5,840,077 A * | 11/1998 | Rowden et al. | 606/119 |
| 6,293,952 B1 * | 9/2001 | Brosens et al. | 606/119 |
| 2005/0107664 A1 | 5/2005 | Kalloo et al. | |
| 2005/0187561 A1* | 8/2005 | Lee-Sepsick et al. | 606/108 |
| 2005/0261714 A1 | 11/2005 | McCartney | |
| 2006/0206064 A1 | 9/2006 | Kagan et al. | |
| 2006/0241344 A1* | 10/2006 | Wilk | 600/114 |
| 2006/0254603 A1* | 11/2006 | Edwards et al. | 128/898 |
| 2007/0112425 A1* | 5/2007 | Schaller et al. | 623/2.37 |
| 2009/0318752 A1* | 12/2009 | Evans et al. | 600/37 |

* cited by examiner

*Primary Examiner* — Gary Jackson
*Assistant Examiner* — Kevin Everage
(74) *Attorney, Agent, or Firm* — John L. Rogitz

(57) ABSTRACT

A transuterine cannula through which an endoscope can be advanced into the peritoneal space to provide visualization of tissue cutting in the peritoneal space pursuant to a vaginal hysterectomy.

26 Claims, 9 Drawing Sheets

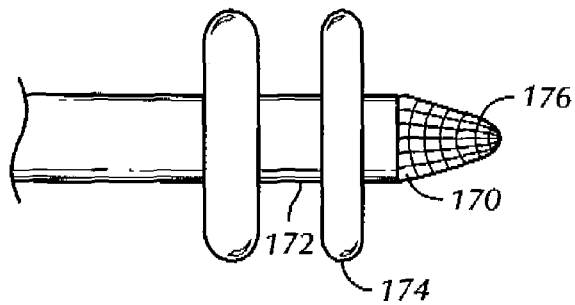
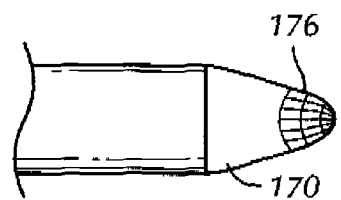
FIG. 11     FIG. 12
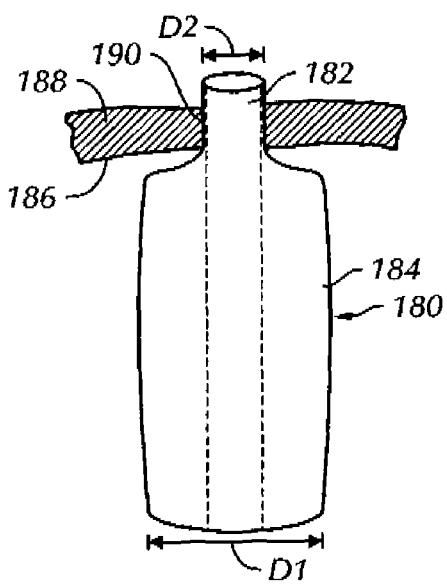
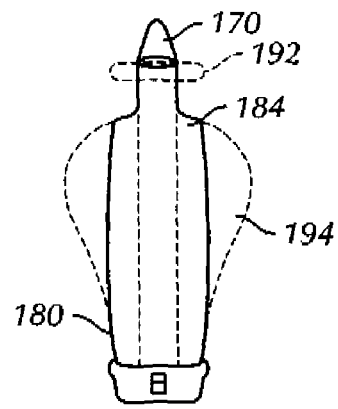
FIG. 13     FIG. 14
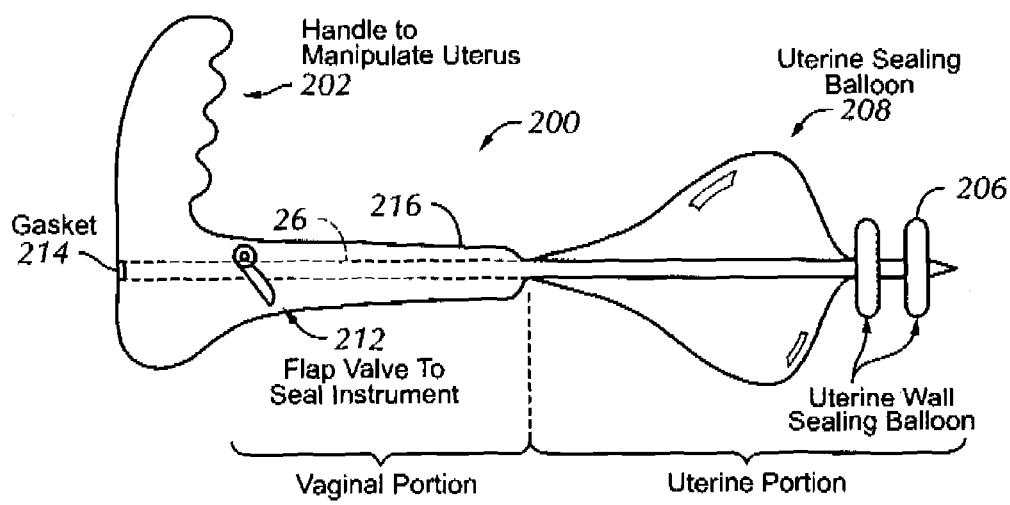
FIG. 15

METHODS AND APPARATUS FOR NATURAL ORIFICE VAGINAL HYSTERECTOMY

This application claims priority from U.S. provisional application Ser. No. 60/867,061, filed Nov. 22, 2006.

FIELD OF THE INVENTION

The present invention relates generally to vaginal hysterectomies.

BACKGROUND OF THE INVENTION

Less invasive surgical procedure for undertaking hysterectomies have become popular, owing to the faster recovery times, improved cosmesis, and lower risks they afford compared to conventional hysterectomies. Least invasive hysterectomy procedures typically involve one of three primary approaches—vaginal hysterectomy, total laparoscopic hysterectomy (TLH), and laparoscopically assisted vaginal hysterectomy (LAVH) with TLH being the least invasive approach. TLH is less invasive than LAVH because it avoids the trauma normally caused by the expansion induced to the vaginal area to permit access of the surgeon's hands to the cervical area.

Difficulty, however, is encountered when employing vaginal, TLH and LAVH techniques due to inherent limitations on visibility, anatomical identification, and the ability to manipulate organs (especially the uterus). In the case of TLH, these limitations are particularly pronounced because of a higher degree of difficulty in securing the uterine arteries and ligaments associated with this approach.

Other limitations associated with vaginal, TLH and LAVH surgical approaches include limited exploratory ability and surgical control. Vaginal, TLH and LAVH approaches can also result in the unnecessary shortening of the vagina due to the limitations discussed above. These difficulties and limitations have slowed the move by surgeons to use the least invasive surgical approach for hysterectomies.

Accordingly, the present invention critically recognizes that it would be advantageous to provide improved methods and apparatus for less invasive hysterectomies, particularly in visualizing interior body structures.

SUMMARY OF THE INVENTION

In one implementation, a cannula, possibly containing an obturator, is directed into the vagina, through the cervix and into the uterus. Then the distal wall (also referred to as "fundus") of the uterus is transversed using a penetrating element at the distal portion of the cannula. The cannula is secured to the wall of the uterus with a gas seal or pair of gas sealing devices and the obturator, if provided, is removed to facilitate the introduction of an endoscope into the cannula and into the abdominal cavity. The abdominal cavity is then insufflated with gas. A luer side valve may be used to insufflate via the cannula. Or, the abdomen can be insufflated prior to cannula insertion via a veress needle or similar device in the pouch of Douglas or abdomen. The uterus with its attached fallopian tubes, arteries, ligaments and connective tissue is located, with or without ovaries, isolated from these structures and removed using instruments placed through the cannula, the working lumen of the endoscope or delivered transvaginally.

Although the embodiments described may be particularly applicable for removal of the uterus, the systems, methods and devices described may also be useful for other operations performed through natural body orifices and the embodiments detailed may have other potential applications for pancreatic, liver and gall bladder, appendix and gastro-intestinal systems as well.

In an aspect, an assembly for transuterine visualization of a transvaginal hysterectomy includes an elongated transuterine cannula configured for advancement through the vagina and uterus to a distal wall of the uterus. A sealing device engaged with the transuterine cannula can engage the cannula with the distal wall. Further, a penetrating element is associated with the transuterine cannula to fenestrate the distal wall to form an opening therein. An endoscope can be advanced through the cannula and the opening in the distal uterine wall into the peritoneal space to provide visualization of anatomical structure in the peritoneal space. A disinfectant can be introduced into the uterus prior to fenestration.

The penetrating element may be established by a distal tip of the transuterine cannula. Or, the penetrating element can be established by a cutting device advanceable through the transuterine cannula.

The transuterine cannula can be secured to the distal wall of the uterus using a gas seal. In some embodiments the transuterine cannula is secured to the distal wall of the uterus using a pair of gas sealing devices. The gas sealing devices can be inflatable balloons.

In non-limiting implementations a veress cannula may be slidably engageable with a lumen of the endoscope to fenestrate the distal uterine wall. A dissecting device may be provided for cutting the anatomical structure in the peritoneal space for which the endoscope provides visualization. In some embodiments one or more of the transuterine cannula and endoscope can articulate while in a patient.

In non-limiting embodiments a vacuum shroud can surround a distal end of the endoscope and can communicate with a source of vacuum to attract the distal wall of the uterus proximally toward the endoscope to facilitate fenestration of the distal wall. A vaginal guide may be provided that is closely received in a vagina of a patient. The guide may be formed with at least one hole slidably supporting the transuterine cannula.

In some embodiments an obturator is disposable in the transuterine cannula to facilitate advancing the transuterine cannula to the distal wall of the uterus. The obturator can have a frusto-conical distal segment terminating in a rounded distal tip, and at least the distal tip bears a bipolar electrode array for fenestrating the distal wall of the uterus.

In some embodiments the transuterine cannula is formed with a distal neck and a shoulder proximal to the neck and adjoined thereto. The shoulder is wider than the neck for abutting an inner surface of the distal wall of the uterus with the neck disposed in the opening thereof.

In some embodiments a uterine stabilizing balloon surrounds a portion of the transuterine cannula and has an inflatable configuration, wherein the stabilization balloon substantially fills the uterus to facilitate manipulation of the uterus, and a deflated configuration, wherein the stabilization balloon is configured to facilitate advancing the transuterine cannula into the uterus.

The cannula and balloon structure may be able to flex within any part of the vagina, cervix, or uterus, allowing for extra uterine manipulation for better antero or retro flexion of the uterus to assist with visualizing structures of the abdomen.

A non-limiting transuterine cannula may define an outer surface and may include at least one working channel external to the outer surface. A vaginal positioning guide that is closely receivable in a vagina can be provided if desired. The guide receives the transuterine cannula therethrough. The vaginal positioning guide can bear at least one tissue dissector for fenestrating the vagina. The vaginal positioning guide can include a balloon that is inflatable to substantially fill the vagina to anchor the guide in the vagina when the transuterine cannula extends therethrough into the uterus.

In another aspect, a transuterine cannula has a cannula body having a length sufficient to advance the transuterine cannula through the vagina of a patient to the distal wall of the uterus of the patient with at least a proximal segment of the transuterine cannula remaining outside the patient's body. At cast one sealing member is engaged with a distal segment of the transuterine cannula to hold the transuterine cannula against the distal wall of the uterus.

The details of the present invention, both as to its structure and operation, can best be understood in reference to the accompanying drawings, in which like reference numerals refer to like parts, and in which:

BRIEF DESCRIPTION OF THE DRAWINGS

FIGS. 11 and 12 are side views of the distal ends of obturators that can be advanced through the transuterine cannula and used to fenestrate the distal wall of the uterus;

FIGS. 13 and 14 are side views of another alternate transuterine cannula with a shoulder stop, with portions shown in phantom;

FIG. 15 is a side view of yet another alternate transuterine cannula with uterine stability balloon and uterine manipulation handle;

DETAILED DESCRIPTION OF THE PREFERRED EMBODIMENT

Figure 1:
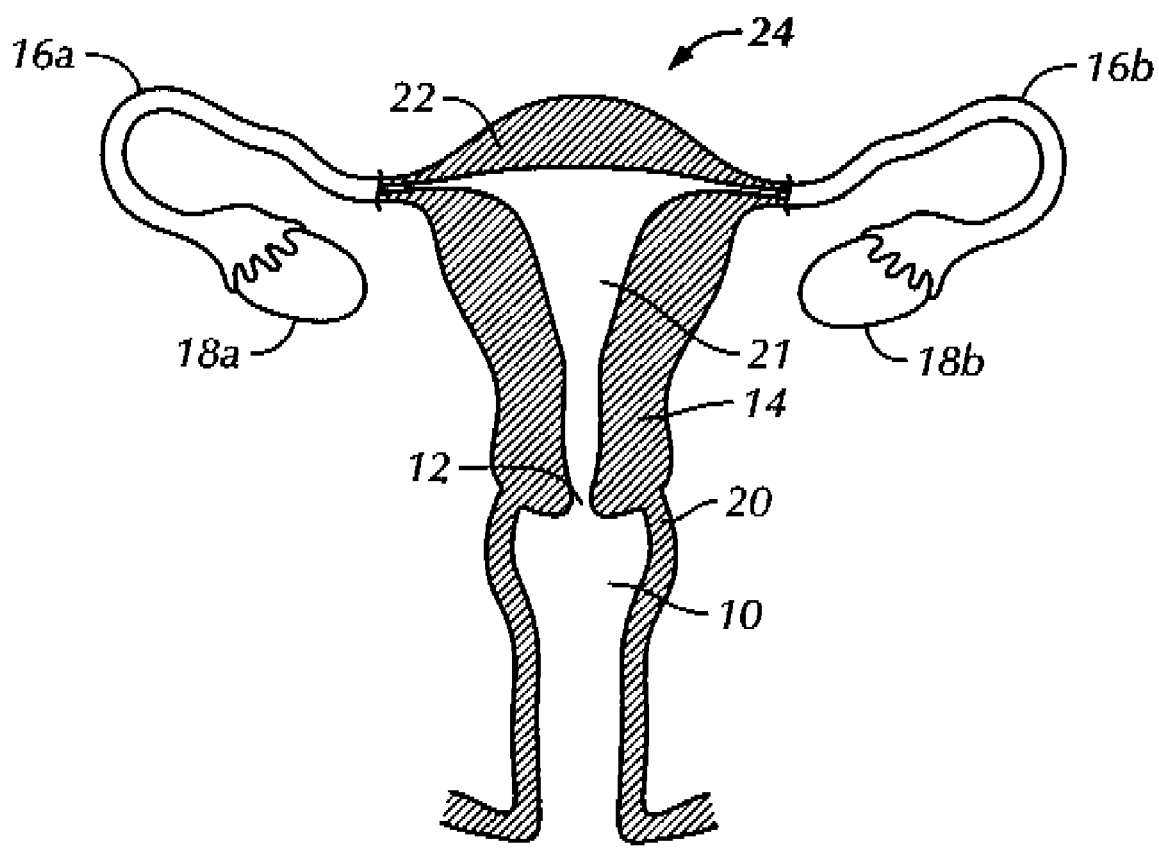
FIG. 1 is an anterior cross sectional view of the uterus.

For perspective, FIG. 1 shows diagram of the female reproductive system including the vagina 10, cervix 12, uterus 14, fallopian tubes 16a and 16b, and ovaries 18a and 18b. The distal portion of the vaginal walls 20 terminate at the cervix 12 which serves as the entrance to the uterus 14 and the uterine cavity 21. This cavity 21 has a distal uterine wall 22 which forms at least the distal portion of the uterus 14. The uterus 14 is joined at its distal end by the fallopian tubes 16a and 16b. These tubes are conduits between the ovaries 18a and 18b at each side of the uterus and the uterine cavity.

Figure 3:
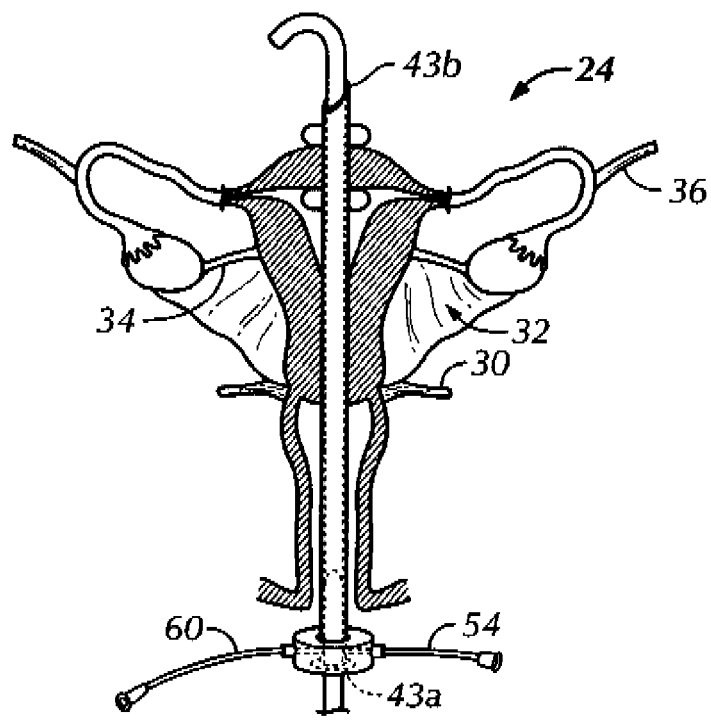
FIG. 3 is a diagrammatic view of the transuterine cannula placed through the wall of the uterus.

As perhaps best shown in FIG. 3, the ovaries are suspended and secured to the lower abdominal cavity 24 with various ligaments such as the uterosacral ligament 30, the broad ligament generally designated 32, the ovarian ligament 34, and the suspensory ligament 36. In addition, blood vessels that supply blood to the reproductive organs are located at various places around the uterus. Typically, most if not all of the ligaments and blood vessels associated with the uterus must be transected to execute a hysterectomy.

Figure 2:
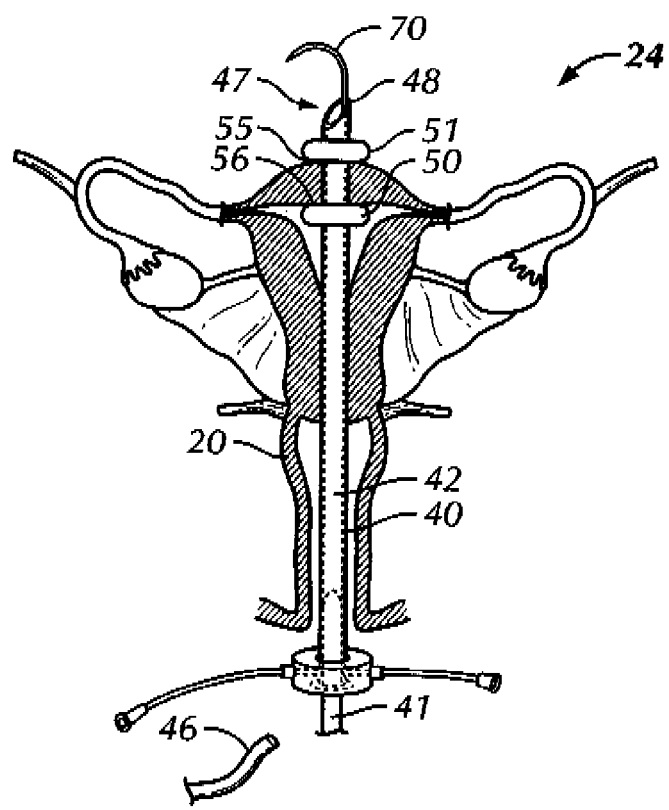
FIG. 2 is a view of the uterus of FIG. 1 with an embodiment of the invention placed into the uterus, with the interior lumens of one non-limiting transuterine cannula shown in phantom.

An embodiment of the invention is shown in FIG. 2 and comprises a transuterine cannula 40 sized for introduction through the vagina 10, cervix 12 and uterus 14 and through the wall 22 of the uterus. The transuterine cannula 40 may be made of axially rigid plastic or metal that is biocompatible and that may be coated with an anti-bacterial agent.

An obturator 41 may be placed through a central lumen 42 of the transuterine cannula 40 to stiffen the transuterine cannula 40 and provide column strength to advance the transuterine cannula assembly into position. The obturator 41 is removable and can be withdrawn from the transuterine cannula 40 after the transuterine cannula is in position. The central lumen 42 of the transuterine cannula is large enough to accommodate a flexible endoscope or laparoscope 46 into the central lumen 42 once the obturator 41 is withdrawn. Transuterine cannulas with central lumens of various sizes can be utilized but preferably the transuterine cannula 40 is large enough to accommodate an endoscope 46 with an outside diameter of between five millimeters (5 mm) and sixteen millimeters (16 mm) and more preferably between 8 mm and 14 mm. Most preferably the central lumen 42 should be large enough to accommodate an endoscope 46 with an outside diameter of up to 12 mm.

Furthermore, the internal diameter of the central lumen 42 preferably is sized similar to the outside diameter of the endoscope 46 so that when the endoscope 46 is placed through the central lumen, the walls of the central lumen 42 effectively seal around the endoscope 46 and inhibit fluids from passing along the outside surface of the endoscope and out the central lumen 42.

Alternatively or in addition, as best shown in FIG. 3 seals 43a and 43b can be positioned at the points where the endoscope 46 exits the proximal and distal portions of the transuterine cannula 40 to respectively seal around the proximal and distal portions of the endoscope and prevent leakage.

Referring back to FIG. 2, in some implementations the distal end 47 of the transuterine cannula 40 may be formed with or may include a penetrating element 48. In the non-limiting embodiment shown, the penetrating element 48 may be a sharpened blade that is angled with respect to the longitudinal axis of the transuterine cannula 40 and that cuts a hole through the uterine wall 22 as the transuterine cannula is rotated and advanced distally against the wall. In other implementations the penetrating element 48 may include a diathermy element that can cauterize and/or cut through uterine tissue. The penetrating element 48 may use other cutting mechanisms including mechanical, chemical, thermo electrical or optical.

Yet again, the transuterine cannula 40 can have a blunt distal end that establishes a tissue separating design that spreads the tissue fibers rather than cutting them. Alternatively a retractor can be used to pull against the superior uterine wall as the transuterine cannula is introduced to prevent perforation of the bowel or some other structure when the trans uterine cannula is inserted through the uterus wall. Further details of such structures are discussed below.

Although not a requirement, the introduction of the transuterine cannula into the patient and subsequent manipulation of reproductive tissues may also be visualized by using fluoroscopy, echo, or other imaging modality.

In some implementations, in addition to or in lieu of the seals 43a, 43b, to secure the transuterine cannula 40 to the distal wall of the uterus the transuterine cannula can have at least one inflatable balloon and preferably two balloons 50 and 51 positioned about the outer surface of the hollow shaft of the transuterine cannula. The balloons are spaced apart by a distance approximately equivalent to the thickness of a uterine wall but this distance can be altered by a sliding mechanism of the balloons which modulates the relative separation between tile balloons.

In any case, an inflation lumen 54 in the transuterine cannula communicates with the inner portions of the balloons 50, 51 and the proximal end of the transuterine cannula. The inflation lumen 54 can be used to inflate the balloons with fluid once the transuterine cannula is in position so that they inflate against the outer 55 and inner 56 surfaces, respectively, of the uterine wall 22. When so inflated the balloons 50, 51 seal around the transuterine cannula 40 so that fluids and more particularly insufflation gas in the abdominal cavity 24 does not leak into the uterine cavity 21 around the transuterine cannula. Alternatively, artificial septums, pads or cloth, sponges or other means may be utilized also to seal the transuterine cannula at the uterine wall.

If desired, the transuterine cannula 40 can also include an insufflation lumen 60 that can be used to insufflate the abdominal cavity 24 with gas. The insufflation lumen 60 is a conduit that communicates with the abdominal cavity 24 at the distal end 47 of the transuterine cannula and terminates at the proximal end of the transuterine cannula so that when the endoscope is placed into the abdominal cavity through the transuterine cannula, gas such as carbon dioxide can be introduced at the proximal end of the insufflation lumen to inflate the abdominal cavity 24. In some embodiments this entails introducing the gas into the cannula and out of a port in the cannula into the lumen 60, which may be defined by an annular space between the endoscope and cannula. The gas inflates the abdominal space 24 and creates sufficient room so that the endoscope can visualize the anatomy and so that instruments introduced into the abdominal cavity 24 can be freely manipulated to accomplish the hysterectomy.

Still further, the transuterine cannula 40 can be loaded with a deployable purse string suture system that could be pulled tight to help to gain a better seal between the uterus and the transuterine cannula or to close the uterine incision if the uterus is not to be removed.

Additionally, a cutting device 70 may be introduced through another separate lumen in the transuterine cannula 40 into the abdominal cavity. The cutting device 70 may be a mechanical cutter, a diathermy cutter, a mono polar, bipolar electrocautery cutter, a laser, or a blade that is used to cut and/or cauterize the ligaments, connective tissue and blood vessels surrounding and attached to the uterus. The cutting device 70 cuts through this attached tissue so that the uterus may be isolated and removed. Alternatively the cutting device may be introduced through a working channel in the endoscope or through the wall of the vagina 20 as discussed further below. Alternatively the cutting device can be introduced through the abdominal wall. Alternatively, a grasper or tissue manipulator can be placed through the central lumen of the endoscope to grasp or manipulate tissue.

The cutting device may alternatively cut and/or ligate so that tissue may be resected and blood vessels can be tied off and occluded at the same time. Therefore the cutting device may also be a ligation device employing ties, sutures, staples, use coagulation diathermy, laser, ultrasound or any energy modality that could induce hemostasis or clips to ligate.

The transuterine cannula 40 described is a relatively rigid device that when positioned as described, facilitates the introduction of the endoscope into the abdominal cavity. The transuterine cannula 40 also facilitates the movement of the uterus and cervix so that these organs can be manipulated to provide the endoscope with a better view of target structures and places the structures around the uterus on a stretch to gain better visualization and simplified cutting and coagulation. The transuterine cannula with its balloons also provides an effective method of sealing around the transuterine cannula body as it exits the uterine wall.

In operation for the removal of the uterus, a transuterine cannula 40 having an obturator 41 inside is placed into the vagina and moved through the cervix and placed against the distal wall of the uterus. As discussed above the uterine wall can be transected and an endoscope advanced through the transuterine cannula 40 and uterine wall for visualization, it being understood that the endoscope is electrically connected to a monitor in the operating room.

To transect the uterine wall the transuterine cannula 40 is manipulated through the uterine wall using a penetrating element positioned at the distal end of the transuterine cannula. The manipulation through the uterine wall may include rotating the transuterine cannula, pushing on the transuterine cannula from the proximal end or alternatively turning on and off the penetrating element. Once the transuterine cannula is positioned across the uterine wall, which can be verified endoscopically or by utilizing marking elements on the body of the transuterine cannula, the obturator is removed and the above-described endoscope or laparoscope or multiple endoscopes (are) is then inserted into the transuterine cannula and advanced to at least the distal portion of the transuterine cannula.

Then sealing elements 43a, 43b, only one of which maybe used and which are positioned about the distal portion of the transuterine cannula, are used to secure the transuterine cannula 40 on the wall of the uterus. Or, as described above balloons 50, 51 are inflated against the proximal and distal surfaces of the uterine wall to sandwich the distal wall of the uterus between the balloons and seal off the inner cavity of the uterus from the abdominal cavity around the transuterine cannula outer wall. Gas is then introduced into the abdominal cavity through an insufflation lumen in the transuterine cannula and the abdominal cavity is inflated to create space so that the uterine structures and anatomy can be directly visualized. Various instruments can be introduced into the abdominal space to ligate, such as endoscopic clip appliers, to coagulate and/or cut various connecting ligaments, fallopian tubes, blood vessels and connective tissue attached to the uterus, or to grasp and manipulate tissue. The uterus is thus isolated from surrounding tissue so that the uterus can be removed. Also, the transuterine cannula system may be deployed through other areas such as the pouch of Douglas, the cul-de-sac) the perineum, colonic/rectal structures.

At this point the uterus can be separated from the vagina and removed through the vagina according to vaginal hysterectomy methods. The removal of the uterus may be assisted by the use of various accessories or instruments that can be introduced through the transuterine cannula, a working lumen of the endoscope or trans-vaginally such as a morcelator system, umbrellas, nets, bags, blades, or hydro- or cryodissection devices.

Also, other energy modalities can be used to destroy tissues such as ultrasound (CUSAR), laser, etc., or tissue ablation modalities may be used, such as chemical morcellation. Alternatively, the transuterine cannula can be removed from the patient and a morcelator system can be introduced through the cervix to remove the uterus. In this case, the morcelator can be placed directly at the cervix and used to pull the uterus down into the morcelator as the uterus is removed.

Figure 4:
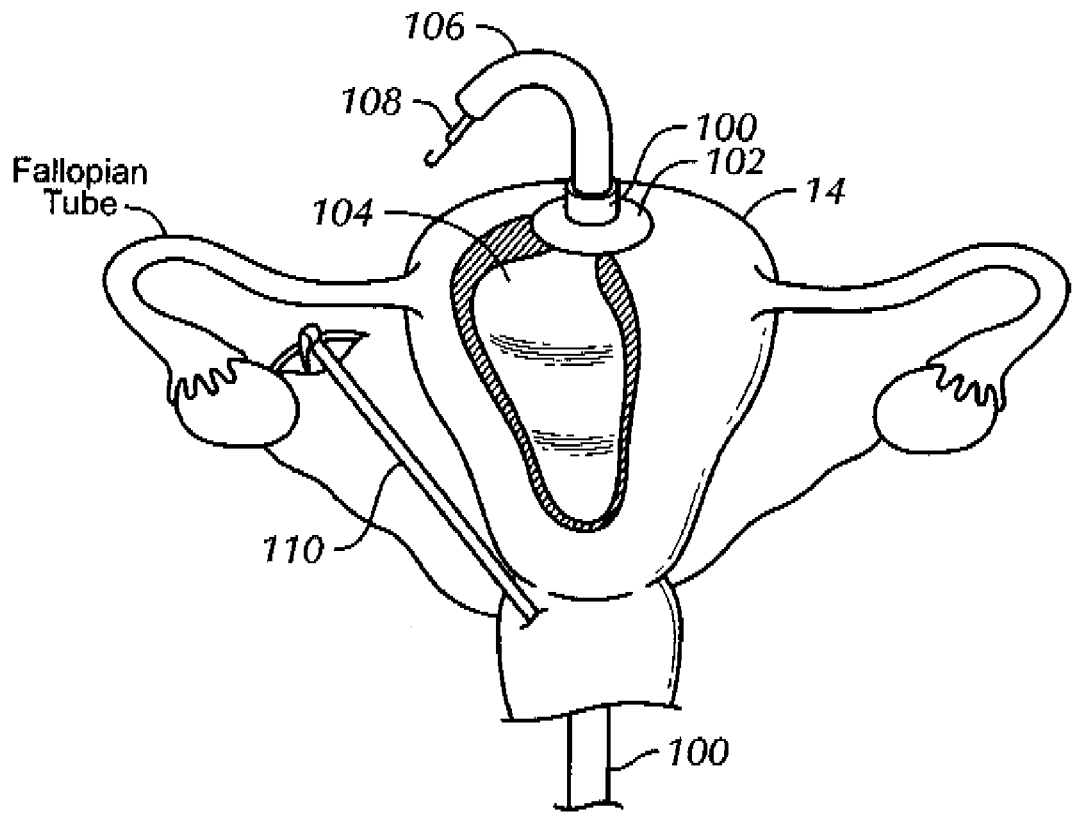
FIG. 4 is a perspective view showing the viewing endoscope emerging through the transuterine cannula past the distal wall of the uterus and into the peritoneal space, and also showing a dissecting device advanced through the vaginal wall to anatomical structure to be transected.

Now referring to FIG. 4 and ensuing figures for additional details, a transuterine cannula 100 is shown advanced through the uterus 14 with the distal end of the cannula 100 shown positioned through the distal wall of the uterus and in the peritoneal space. The transuterine cannula 100 may be identical in configuration and operation to the transuterine cannula 40 discussed above, and/or it may embody the following exceptions. A distal anchoring balloon 102 may surround the distal segment of the transuterine cannula 100 as shown and may be inflated once inside the peritoneal space to hold the transuterine cannula 100 in place. Also, an enlarged proximal balloon 104, referred to herein as a "stabilizing" balloon, may surround the transuterine cannula 100 and can be inflated when inside the uterus as shown to substantially fill the uterus. The proximal balloon 104 has an inflatable configuration, wherein the balloon substantially fills the uterus to facilitate manipulation of the uterus, and a deflated configuration, wherein the balloon is configured to facilitate advancing the transuterine cannula 100 into the uterus. It is to be understood that a third, smaller sealing balloon similar to the proximal balloon 50 shown in FIG. 2 may be disposed between the stabilization balloon 104 and the inside surface of the distal wall of the uterus if desired, or the stabilization balloon 104 may be used in lieu of the proximal balloon 50.

FIG. 4 shows that an endoscope 106 can be advanced through the transuterine cannula 100 to provide visualization of the peritoneal cavity as shown. Preferably, the endoscope is articulate, meaning it can be bent by means of, e.g., a manipulation wire embedded in the endoscope near its distal end and extending through the endoscope to a manipulator handle as more fully described below. In this way, the endoscope can be bent in a desired direction to visualize, e.g., the Fallopian tube as shown in FIG. 4. The endoscope 106 may define one or more working channels, and an instrument such as but not limited to a ligation band 108 maybe advanced through the working channel to, e.g., ligate a Fallopian tube as shown in FIG. 4.

A dissecting device 110, which may be a bipolar transection device, may be advanced through the working channel of the endoscope 106 or, as shown in FIG. 4, through a vaginal wall to an anatomical structure (e.g., the Fallopian tube) to be cut in the peritoneal space. In this latter approach (i.e., through the vaginal wall) the dissecting device 110 may be advanced through the vaginal positioning guide shown in FIGS. 18-20 and discussed at greater length below. In any case, it will readily be appreciated that the endoscope 106 extending through the transuterine cannula 100 provides visualization to a surgeon operating the dissecting device 110.

Figure 5:
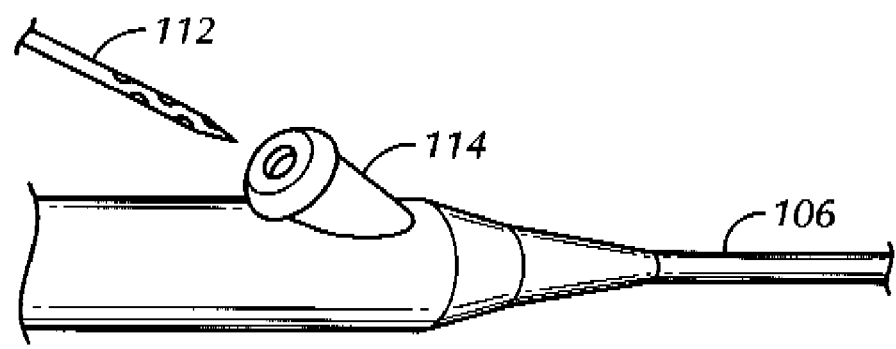
FIG. 5 is a perspective view of a veress cannula being advanced into the working channel of the endoscope prior to engaging the endoscope with the transuterine cannula of FIG. 4.

FIG. 5 illustrates one non-limiting structure that can be used in lieu of the angled blade-like distal end 47 of the transuterine cannula 40 shown in FIG. 2 to fenestrate the distal wall of the uterus to position the transuterine cannula 100 as shown in FIG. 4. A veress cannula 112 can be advanced into a working channel 114 of the endoscope 106 through a shunt lumen as shown, and then the endoscope 106 advanced through the transuterine cannula 100 to the inside surface of the distal wall of the uterus. The veress cannula 112 is then advanced out of the endoscope 106 and manipulated to fenestrate the uterus, with the distal segment of the transuterine cannula 100 then being advanced through the fenestration to permit manipulation of the endoscope 106 into the position shown in FIG. 4. The abdomen may be insufflated with, e.g., carbon dioxide by porting gas through the veress cannula 112, or the working channel of the endoscope, or indeed through the transuterine cannula 100.

Figure 6:
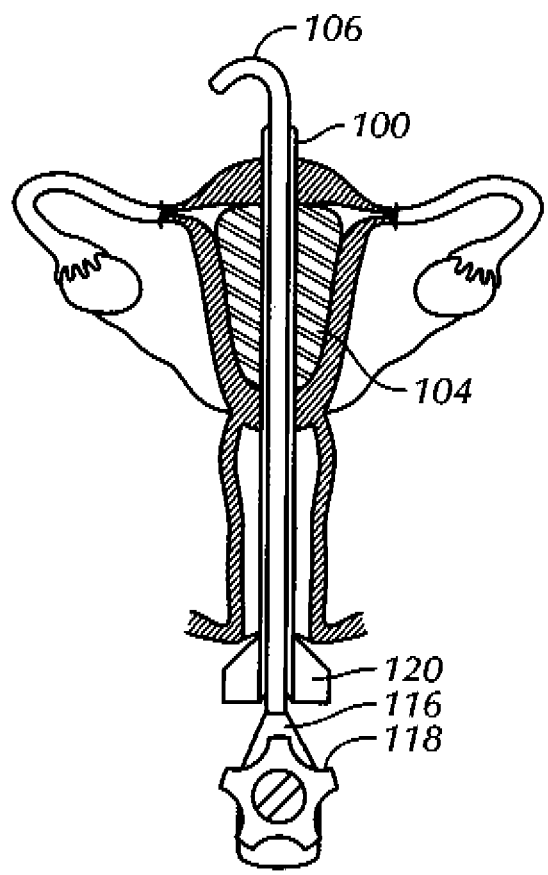
FIG. 6 is a cut-away view showing the transuterine cannula of FIG. 4 advanced through the distal wall of the uterus and the endoscope bent for retrograde visualization, with the scaling balloons omitted for clarity.
Figure 7:
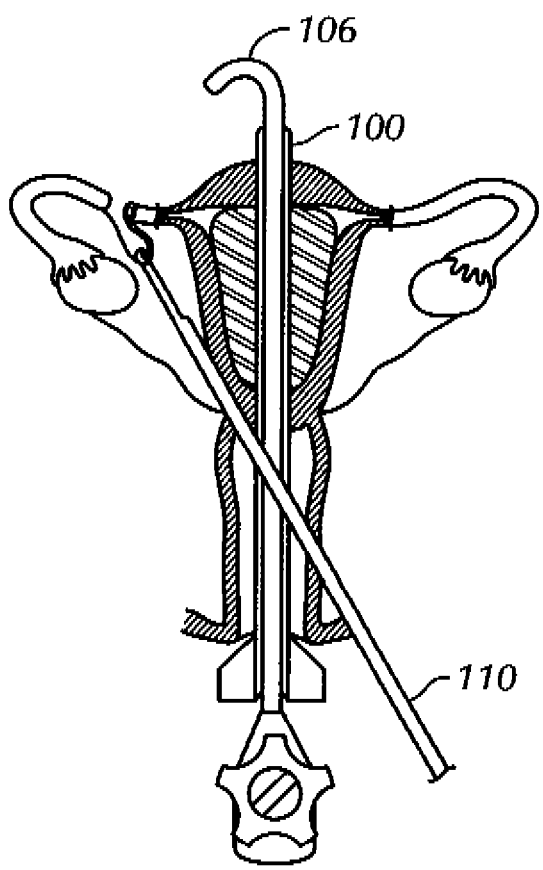
FIG. 7 is a cut-away view illustrating the use of the transuterine cannula with the transvaginal dissecting device shown in FIG. 4.

FIGS. 6 and 7 illustrate additional details of the transuterine cannula 100 and endoscopic 106. The endoscope 106 may be provided with a proximal handle 116 that rotatably bears a manipulating wheel 118. The wheel 118 maybe attached to the above-discussed wire, so that a surgeon can turn the wheel 118 to bend the distal segment of the endoscope 106 as shown in FIG. 6. Also, the transuterine cannula 100 may be formed with a proximal hub 120 that can likewise be manipulated by a surgeon, it being understood that the hub 120 and wheel 118 are outside the patient when the assembly is positioned as shown in FIG. 4, 6, and 7. The surgeon can manipulate the proximal hub 120 to move the transuterine cannula 100, and owing to the cooperation between the stabilization balloon 104 and the uterus, the surgeon can move the uterus somewhat.

FIG. 7 shows schematically that the dissecting device 110 can be manipulated under visualization provided by the endoscope 106 to cut anatomical structure in the peritoneal space. In the case shown, the broad ligament is being cut by the dissecting device 110. The dissection may be inspected by means of the endoscope 106 to ensure acceptable hemostasis. From below, the uterine arteries can then be transected and the uterus subsequently retrieved through the vagina in accordance with vaginal hysterectomy principles.

Figure 8:
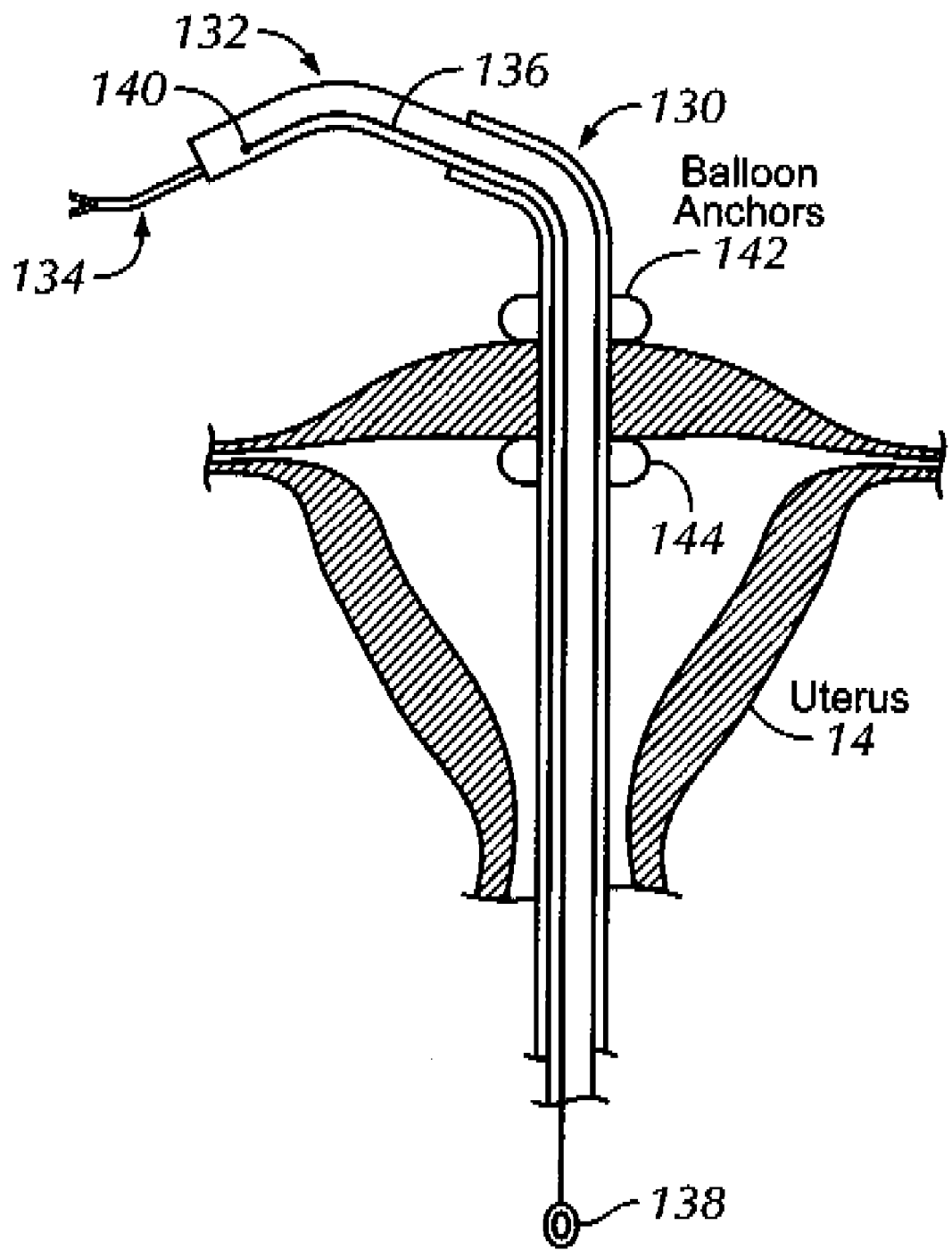
FIG. 8 is a side view of a transuterine cannula with endoscope and instrument in the peritoneal space, illustrating that all three components can be articulated during use.

FIG. 8 illustrates that one or more of a transuterine cannula 130, an endoscope 132 extending through the transuterine cannula 130, and surgical instrument 134 extending through the endoscope 132 can be articulated, i.e., bent when positioned in a patient as desired to provide visualization of a target location. By way of illustration, an articulation wire 136 can extend through a channel of the endoscope 132 from a manipulator wheel 138 outside the patient's body to a distal location 140 on the endoscope 132, where the wire 136 is fastened. The wheel 138 can be manipulated to pull the wire 136 to bend the endoscope 132 as shown, and then released to allow the material bias of the endoscope 132 to straighten the endoscope. It is to be understood that similar articulation structure can be provided for the transuterine cannula 130 and surgical instrument 134. Distal and proximal balloon anchors 142, 144 that are substantially identical in configuration and operation to the balloons 50, 51 shown in FIG. 2 can also be provided on the transuterine cannula 130 to engage the transuterine cannula 130 with the uterus 14.

In non-limiting implementations, the transuterine cannula 130 has two degrees of freedom, namely, rotation and bending. In contrast, the endoscope 132 can have three degrees of freedom, namely, rotation, translation in the proximal and distal dimension through the transuterine cannula 130, and bending. Likewise, the surgical instrument 134 can have three degrees of freedom, namely, rotation, translation in the proximal and distal dimension through the endoscope 132, and bending. In non-limiting implementations the surgical instrument 134 may be, e.g., a scissor, grasper, dissector, electrocautery probe, tissue welder, clip applicator, or ligature applicator.

Figure 9:
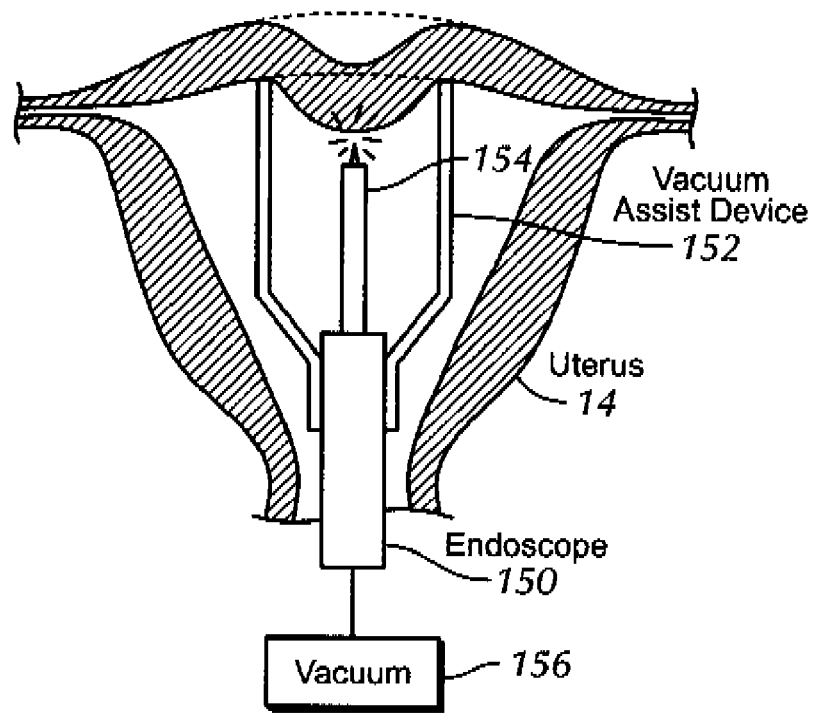
FIG. 9 shows an alternate endoscope that may be used with the present transuterine cannula to attract the distal wall of the uterus inward prior to fenestrating the distal wall.

FIG. 9 shows that an endoscope 150 can be engaged at its distal end with a vacuum shroud 152 that is radially continuous, so that the shroud 152 can be advanced against the distal wall of the uterus as shown and a vacuum induced in the shroud through a lumen of the endoscope 150 to draw the distal wall toward a fenestration instrument 154, which can be advanced through and distally beyond the working channel of the endoscopic 150 as shown to fenestrate the inwardly-drawn distal wall. To this end, the interior of the vacuum shroud 152 communicates with a source 156 of vacuum through the lumen of the endoscope. The fenestration instrument 154 may be, e.g., a bipolar transection device.

With this structure, a vacuum can be drawn in the shroud 152 to urge the distal wall of the uterus against the fenestration instrument 154 to fenestrate the distal wall while reducing the risk that tissue beyond the distal wall in the peritoneal space might unintentionally be damaged.

Figure 10:
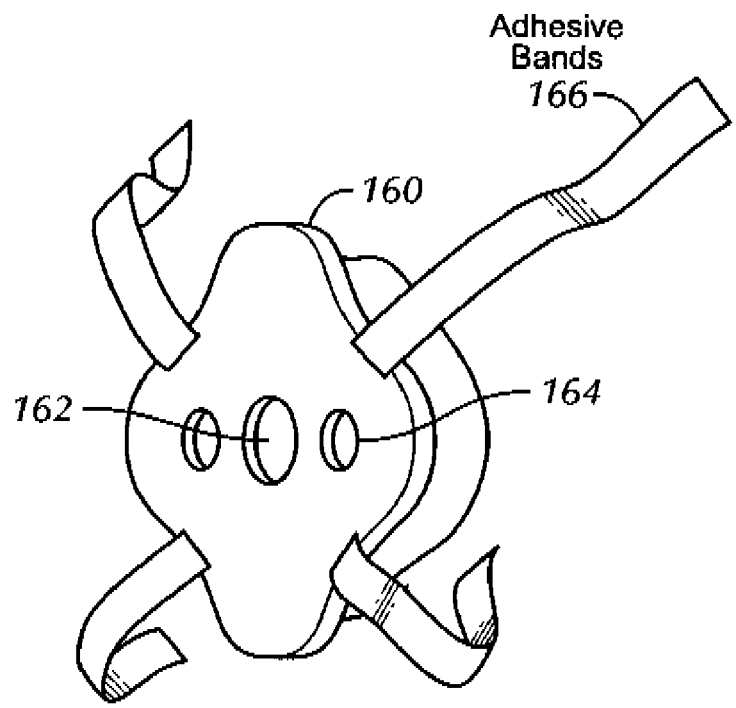
FIG. 10 is a perspective view of a vaginal guide through which the present transuterine cannula may be advanced.

FIG. 10 shows a preferably single-piece plastic vaginal guide 160 that is shaped and sized for being closely received in a vagina of a patient. The guide 160 is formed with a central hole 162 sized to closely receive a transuterine cannula therethrough in slidable support, and additional holes 164 may be formed in the guide for slidably receiving, e.g., the dissecting device 110 shown in FIG. 7. Adhesive bands 166 can be attached to the guide 160 as shown and with the patient's skin to hold the guide in place at the vaginal opening. The guide 160 can be made of a soft elastomer, and it stabilizes the vaginal orifice during hysterectomy while providing access portals and preventing injury that might otherwise occur due to repeated insertion and manipulation of instruments as described above. The guide 160 also provides a resting point and fulcrum for, e.g., the transuterine cannula described herein.

FIGS. 11 and 12 show that an obturator 170 of the present invention may be advanced past the distal opening of a transuterine cannula 172 with sealing balloons 174 to fenestrate the distal wall of the uterus. Specifically, the obturator 170 may have a frusto-conical distal segment terminating in a rounded distal tip as shown, and the entire frusto-conical distal segment (FIG. 11) or only the rounded distal tip (FIG. 12) may bear an electrode array 176. The array 176 can be energized via an energization wire extending through the transuterine cannula 172 for fenestrating the distal wall of the uterus and at the same time cauterizing the cut tissue.

FIGS. 13 and 14 show an alternate transuterine cannula 180 formed with a distal neck 182 and a shoulder 184 proximal to the neck 182 and adjoined thereto. The shoulder 184 has a larger diameter D1 than the diameter D2 of the neck 182. Thus, the shoulder 184 is wider than the neck 182 for abutting the inner surface 186 of the distal wall 188 of the uterus with the neck 182 disposed in the opening 190 of the wall made by one of the above-described fenestration devices. With this structure, the diameter of the opening 190 is reduced while the portion of the transuterine cannula 180 residing in the uterus is relatively large to aid in manipulating the uterus. Also, the shoulder 184 self-limits the depth of penetration of the transuterine cannula 180 into the peritoneal space.

FIG. 14 illustrates this latter principle in greater detail. Distal and proximal sealing balloons 192, 194 that may be substantially identical in configuration and operation to the balloons 102, 104 shown in FIG. 4 can be provided on the transuterine cannula 180 and inflated on opposite sides of the distal uterine wall. The above-described obturator 170 can then be advanced into the wall to fenestrate it, at which point the neck 182 of the transuterine cannula 180 can be pushed through the fenestration with the shoulder 184 abutting the inner surface of the distal uterine wall to limit the distance the neck 192 can be pushed into the peritoneal space.

FIG. 15 shows a transuterine cannula 200 that has a proximal handle 202 outside the patient that can be manipulated to move the uterus as desired. In the embodiment shown in FIG. 15, a uterine portion 204 of the transuterine cannula 200 may include proximal and distal sealing balloons 206 for sealing against opposite sides of the distal uterine wall, and a stabilization balloon 208 for substantially filling the uterus when inflated. The balloons 206, 208 can be inflated by porting inflation fluid through an inflation lumen 210 of the transuterine cannula 200, which can be closed off after inflation using a flap valve 212 on the handle 202 as shown to hold the balloons 206, 208 in the inflated configurations. If desired, the inflation lumen 212 can be connected to an external source of vacuum and a proximal gasket 214 can be provided around the inside periphery of the proximal end of the inflation lumen 210 to establish a seal between the source of vacuum and lumen. A narrow segment 216 of the handle 202 may be disposed in the vagina when the transuterine cannula 200 is positioned as intended with the sealing balloons 206 inflated on opposite sides of the distal uterine wall.

Figure 16:
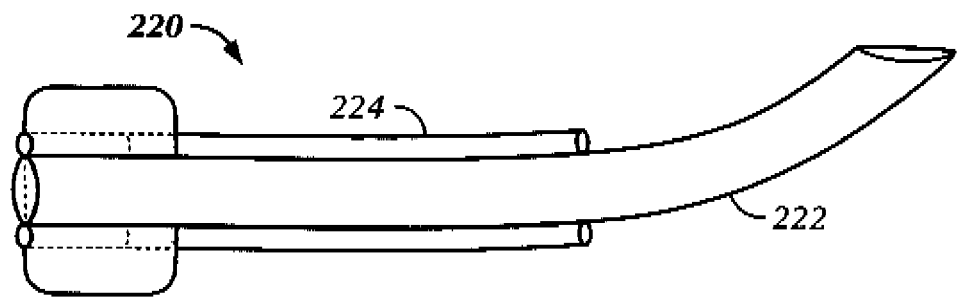
FIGS. 16 and 17 are side views of alternate transuterine cannulae with exterior lumina.
Figure 17:
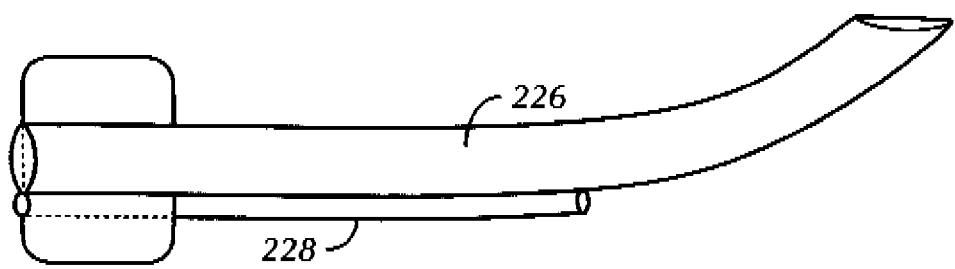

FIG. 16 shows a transuterine cannula 220 with an outer surface 222, and two external tubes 224 forming lumens extending along the outer surface 222 to provide working channels external to the transuterine cannula 220. FIG. 17 shows a transuterine cannula 226 with a single external tube 228. The transuterine cannulas shown in FIGS. 16 and 17 can have bevelled distal tips as shown for cutting tissue, and are shown in slightly articulated configurations.

Figure 18:
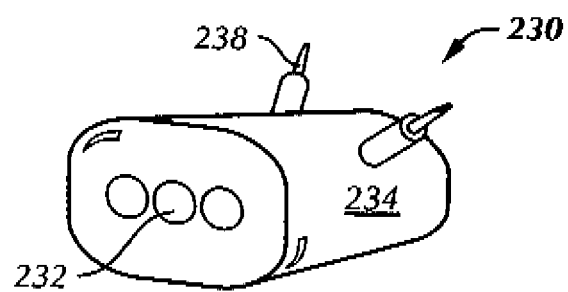
FIGS. 18-20 are perspective, side, and schematic views, respectively, of a vaginal positioning guide with transvaginal tissue dissectors, with any one of the transuterine cannulae shown in the preceding figures being advanceable through a central channel of the vaginal positioning guide into the uterus.
Figure 19:
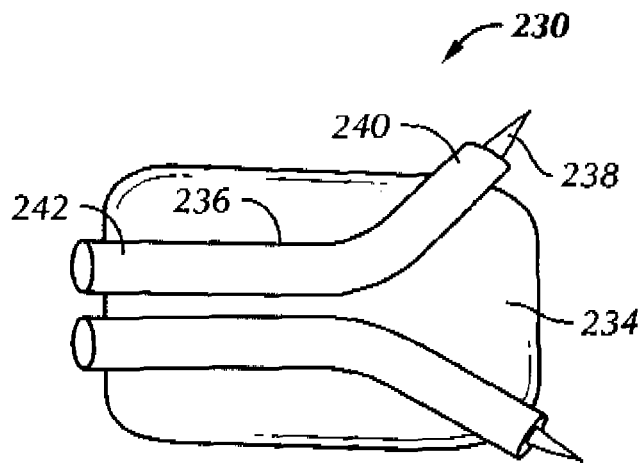
Figure 20:
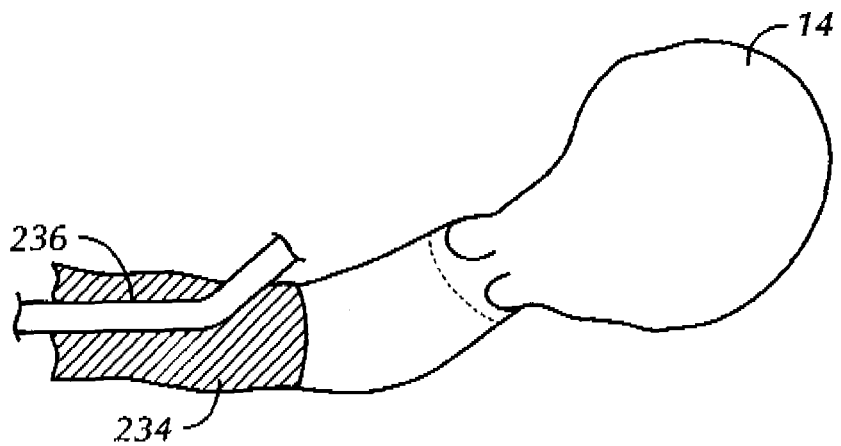

FIGS. 18-20 show a vaginal positioning guide 230 that is closely receivable in a vagina for receiving one of the above-described transuterine cannulae through a central lumen 232 of the guide 230. Essentially, the vaginal positioning guide 230 includes a balloon 234 that is inflatable to substantially fill the vagina to anchor the guide in the vagina when the transuterine cannula extends through the central lumen 232 and into the uterus 14.

As shown, the guide 230 may be constructed with one and preferably two lateral lumens 236. The lateral lumens 236 can be established by respective tubes that are disposed in the balloon 234. Respective tissue dissectors 238 can extend through the lateral lumens 236 for fenestrating the vagina, so that, e.g., one or more of the dissectors 238 can be used as the dissecting device 110 shown in FIG. 7. Or, the dissectors 238 can be removed after fenestrating the vagina and a substitute dissecting device 110 advanced through the lateral lumen and vaginal wall to an anatomical structure to be dissected as described above. If desired, as best shown in FIG. 19 the distal portion 240 of one or both lateral lumens 236 can be angled outwardly from the axis of the respective proximal portion 242 as shown.

Figure 21:
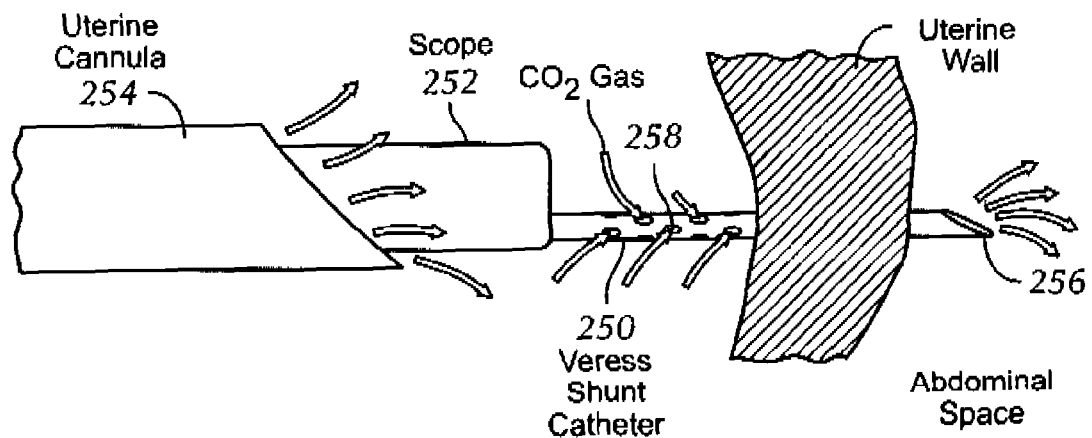
FIG. 21 is a schematic side view of the distal portion of an endoscope with perforated shunt veress cannula.

FIG. 21 shows a multiperforated veress shunt cannula 250 that is slidably engageable with a lumen of an endoscope 252 that is in all essential respects identical in construction and configuration to the endoscopes described previously and that consequently nay be engaged with a transuterine cannula 254 as set forth above. The shunt cannula 250 is a sharpened distal end 256 as shown and multiple holes 258. The shunt cannula 250 accordingly may be advanced through the uterine wall as shown and into the abdominal cavity to establish a pathway for fluid (e.g., CO2) communication from the uterine space of a patient to the abdominal cavity of the patient.

While the particular METHODS AND APPARATUS FOR NATURAL ORIFICE VAGINAL HYSTERECTOMY are herein shown and described in detail, it is to be understood that the subject matter which is encompassed by the present invention is limited only by the claims.

What is claimed is:

1. An assembly for transuterine visualization of a transvaginal hysterectomy, comprising:
    an elongated transuterine cannula configured for advancement through the vagina and uterus to a distal wall of the uterus;
    at least one sealing device engaged with the transuterine cannula to engage the cannula with the distal wall;
    at least one penetrating element associated with the transuterine cannula to fenestrate the distal wall to form an opening therein;
    at least one endoscope advanceable through the cannula and opening in the distal wall of the uterus into a peritoneal space to provide visualization of anatomical structure in the peritoneal space; and
    a vaginal guide shaped and sized for being closely received in a vagina of a patient, the guide being formed with a hole sized to closely receive the transuterine cannula therethrough, in slidable support, the guide further including one or more bands attachable with the patient's skin to hold the guide in place at the vaginal opening, the guide being made of a soft elastomer, the guide stabilizing the vaginal orifice during hysterectomy while providing access portals and preventing injury that might otherwise occur due to repeated insertion and manipulation of instruments into the patient, the guide also providing a resting point and fulcrum for the transuterine cannula.

2. The assembly of claim 1, further comprising a veress cannula slidably engageable with a lumen of the endoscope.

3. The assembly of claim 1, further comprising a dissecting device for cutting the anatomical structure in the peritoneal space for which the endoscope provides visualization.

4. The assembly of claim 1, wherein one or more of the transuterine cannula and endoscope can articulate while in a patient.

5. The assembly of claim 1, comprising a vacuum shroud surrounding a distal end of the endoscope and communicating with a source of vacuum to attract the distal wall of the uterus toward the endoscope to facilitate fenestration of the distal wall.

6. The assembly of claim 1, comprising an obturator disposable in the transuterine cannula to facilitate advancing the transuterine cannula to the distal wall of the uterus.

7. The assembly of claim 6, wherein the obturator has a frusto-conical distal segment terminating in a rounded distal tip, and at least the distal tip bears a bipolar electrode array for fenestrating the distal wall of the uterus.

8. The assembly of claim 1, wherein the transuterine cannula is formed with a distal neck and a shoulder proximal to the neck and adjoined thereto, the shoulder being wider than the neck for abutting an inner surface of the distal wall of the uterus with the neck disposed in the opening thereof.

9. The assembly of claim 1, comprising a uterine stabilizing balloon surrounding a portion of the transuterine cannula and having an inflatable configuration, wherein the stabilization balloon substantially fills the uterus to facilitate manipulation of the uterus, and a deflated configuration, wherein the stabilization balloon is configured to facilitate advancing the transuterine cannula into the uterus.

10. The assembly of claim 1, wherein the transuterine cannula defines an outer surface and includes at least one working channel external to the outer surface.

11. The assembly of claim 1, the vaginal positioning guide bearing at least one tissue dissector for fenestrating the vagina.

12. The assembly of claim 11, wherein the vaginal positioning guide includes a balloon inflatable to substantially fill the vagina to anchor the guide in the vagina when the transuterine cannula extends therethrough into the uterus.

13. The assembly of claim 1, wherein the penetrating element is established by a distal tip of the transuterine cannula.

14. The assembly of claim 1, wherein the penetrating element is established by a cutting device advanceable through the transuterine cannula.

15. The assembly of claim 1, wherein the transuterine cannula is secured to the distal wall of the uterus using a gas seal.

16. The assembly of claim 15, wherein the transuterine cannula is secured to the distal wall of the uterus using a pair of gas sealing devices.

17. The assembly of claim 16, wherein the gas sealing devices are inflatable balloons.

18. The assembly of claim 1, wherein at least the cannula can articulate to facilitate antero- and retro-deflexion to facilitate manipulation of the uterus.

19. The assembly of claim 1, further comprising a multi-perforated veress shunt cannula slidably engageable with a lumen of the endoscope to establish a pathway for fluid communication from the uterine space of a patient to the abdominal cavity of the patient.

20. A method for conducting a hysterectomy on a patient, comprising:
    insufflating the abdominal cavity;
    advancing a transuterine cannula into the vagina of the patient, through the cervix and into the uterus;
    securing the transuterine cannula to the distal wall of the uterus;
    fenestrating the distal wall of the uterus;
    advancing an endoscope through the transuterine cannula into the abdominal cavity of the patient;
    viewing at least portions of the uterus with attached anatomical structures using the endoscope; and
    removing at least the uterus using at least one instrument placed through the transuterine cannula and/or a working lumen of the endoscope and/or delivered transvaginally.

21. The method of claim 20, wherein the transuterine cannula is advanced against the distal wall with an obturator contained in the transuterine cannula.

22. The method of claim 20, wherein the transuterine cannula is secured to the distal wall using a gas seal.

23. The method of claim 20, wherein the transuterine cannula is secured to the distal wall using a pair of gas sealing devices.

24. The method of claim 23, wherein the gas sealing devices are inflatable balloons.

25. The method of claim 20, wherein the distal wall is transversed using a penetrating element at the distal portion of the transuterine cannula.

26. The method of claim 20, comprising introducing a disinfectant into the uterus prior to fenestrating the distal wall.

* * * * *